United States Patent
Viola et al.

(10) Patent No.: US 7,326,232 B2
(45) Date of Patent: Feb. 5, 2008

(54) SURGICAL STAPLING APPARATUS AND METHOD

(75) Inventors: Frank J. Viola, Sandy Hook, CT (US); David Ivanko, San Diego, CA (US)

(73) Assignee: Tyco Healthcare Group LP, North Haven, CT (US)

( * ) Notice: Subject to any disclaimer, the term of this patent is extended or adjusted under 35 U.S.C. 154(b) by 0 days.

(21) Appl. No.: 11/357,148

(22) Filed: Feb. 17, 2006

(65) Prior Publication Data

US 2006/0138193 A1 Jun. 29, 2006

Related U.S. Application Data

(62) Division of application No. 10/490,517, filed as application No. PCT/US2002/31963 on Oct. 4, 2002, now Pat. No. 7,032,799.

(60) Provisional application No. 60/327,369, filed on Oct. 5, 2001.

(51) Int. Cl.
*A61B 17/068* (2006.01)

(52) U.S. Cl. ............ 606/219; 227/19; 227/175.1; 227/176.1

(58) Field of Classification Search ............ 227/176.1, 227/178.1, 19, 175.1, 180.1; 606/219
See application file for complete search history.

(56) References Cited

U.S. PATENT DOCUMENTS

| | | | |
|---|---|---|---|
| 960,300 A | 6/1910 | Fischer | |
| 2,301,622 A | 11/1942 | Hambrecht | |
| 2,853,074 A | 9/1958 | Olson | |
| 2,874,384 A | 2/1959 | Krone | |
| 2,891,250 A | 6/1959 | Hirata | |
| 3,079,606 A | 3/1963 | Bobrov et al. | |
| 3,080,564 A | 3/1963 | Strekopov et al. | |
| 3,252,643 A | 5/1966 | Strekopov et al. | |
| 3,269,630 A | 8/1966 | Fleischer | |
| 3,275,211 A | 9/1966 | Hirsch et al. | |
| 3,278,107 A | 10/1966 | Rygg | |
| 3,315,863 A | 4/1967 | O'Dea | |
| 3,499,591 A | 3/1970 | Green | |
| 3,589,589 A | 6/1971 | Akopov et al. | |
| 3,598,299 A | 8/1971 | Johnson | |
| 3,692,224 A | 9/1972 | Astafiev et al. | |
| 3,795,034 A | 3/1974 | Strekopov et al. | |
| 3,889,683 A | 6/1975 | Kapotanov et al. | |
| 3,935,981 A | 2/1976 | Akopov et al. | |
| 3,949,923 A | 4/1976 | Akopov et al. | |
| 3,973,709 A | 8/1976 | Akopov et al. | |
| 4,047,654 A | 9/1977 | Alvarado | |

(Continued)

FOREIGN PATENT DOCUMENTS

EP 0514185 A1 11/1992

(Continued)

*Primary Examiner*—Scott A. Smith

(57) ABSTRACT

The present disclosure is directed to staple-gap adjustment members for use in surgical stapling apparatus and methods. A gap adjustment member includes one or more bearing portions sharing a common rotational axis and one or more cam surface portions having a periphery with at least two different points along the periphery, with each point along the periphery having a different radius from the rotational axis. The one or more cam surface portions can have a central axis parallel to and spaced a distance from the rotational axis of the one or more bearing portions.

8 Claims, 18 Drawing Sheets

U.S. PATENT DOCUMENTS

| | | |
|---|---|---|
| 4,111,206 A | 9/1978 | Vishnevsky et al. |
| 4,162,678 A | 7/1979 | Fedetov et al. |
| 4,216,890 A | 8/1980 | Akopov et al. |
| 4,216,891 A | 8/1980 | Behlke |
| 4,272,002 A | 6/1981 | Moshofsky |
| 4,290,542 A | 9/1981 | Fedetov et al. |
| 4,296,881 A | 10/1981 | Lee |
| 4,316,468 A | 2/1982 | Klieman et al. |
| 4,317,105 A | 2/1982 | Sinha et al. |
| 4,325,376 A | 4/1982 | Klieman et al. |
| 4,378,901 A | 4/1983 | Akopov et al. |
| 4,397,311 A | 8/1983 | Kanshin et al. |
| 4,442,964 A | 4/1984 | Becht |
| 4,453,661 A | 6/1984 | Genyk et al. |
| 4,470,533 A | 9/1984 | Schuler |
| 4,477,007 A | 10/1984 | Foslien |
| 4,485,811 A | 12/1984 | Chernousov et al. |
| 4,527,724 A | 7/1985 | Chow et al. |
| 4,550,870 A | 11/1985 | Krumme et al. |
| 4,570,633 A | 2/1986 | Golden |
| 4,585,153 A | 4/1986 | Failla et al. |
| 4,596,351 A | 6/1986 | Fedetov et al. |
| 4,605,001 A | 8/1986 | Rothfuss et al. |
| 4,607,636 A | 8/1986 | Kula et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,648,542 A | 3/1987 | Fox et al. |
| 4,684,051 A | 8/1987 | Akopov et al. |
| 4,741,336 A | 5/1988 | Failla et al. |
| 4,784,137 A | 11/1988 | Kulik et al. |
| 4,805,823 A | 2/1989 | Rothfuss |
| 4,848,637 A | 7/1989 | Pruitt |
| 4,863,088 A | 9/1989 | Redmond et al. |
| 4,892,244 A | 1/1990 | Fox et al. |
| 4,930,503 A | 6/1990 | Pruitt |
| 4,991,764 A | 2/1991 | Mericle |
| 5,005,754 A | 4/1991 | Vam Overloop |
| 5,018,657 A | 5/1991 | Pedlick et al. |
| 5,065,929 A | 11/1991 | Schulze et al. |
| 5,074,454 A | 12/1991 | Peters |
| 5,083,695 A | 1/1992 | Foslien et al. |
| 5,111,987 A | 5/1992 | Moeinzadeh et al. |
| 5,129,570 A | 7/1992 | Schulze et al. |
| 5,137,198 A | 8/1992 | Nobis et al. |
| 5,141,144 A | 8/1992 | Foslien et al. |
| 5,170,925 A | 12/1992 | Madden et al. |
| 5,172,845 A | 12/1992 | Tejeiro |
| 5,180,092 A | 1/1993 | Crainich |
| 5,188,274 A | 2/1993 | Moeinzadeh et al. |
| 5,205,459 A | 4/1993 | Brinkerhoff et al. |
| 5,240,163 A | 8/1993 | Stein et al. |
| 5,263,629 A | 11/1993 | Trumbull et al. |
| RE34,519 E | 1/1994 | Fox et al. |
| 5,275,322 A | 1/1994 | Brinkerhoff et al. |
| 5,275,323 A | 1/1994 | Schulze et al. |
| 5,285,945 A | 2/1994 | Brinkerhoff et al. |
| 5,292,053 A | 3/1994 | Bilotti et al. |
| 5,307,976 A | 5/1994 | Olson et al. |
| 5,312,024 A | 5/1994 | Grant et al. |
| 5,332,142 A | 7/1994 | Robinson et al. |
| 5,344,061 A | 9/1994 | Crainich |
| 5,364,003 A | 11/1994 | Williamson, IV |
| 5,376,095 A | 12/1994 | Ortiz |
| 5,381,943 A | 1/1995 | Allen et al. |
| 5,383,880 A | 1/1995 | Hooven |
| 5,395,033 A | 3/1995 | Byrne et al. |
| 5,395,034 A | 3/1995 | Allen et al. |
| 5,397,324 A | 3/1995 | Carroll et al. |
| 5,405,073 A | 4/1995 | Porter |
| 5,415,334 A | 5/1995 | Williamson, IV et al. |
| 5,415,335 A | 5/1995 | Knodell, Jr. |
| 5,417,361 A | 5/1995 | Williamson, IV |
| 5,431,323 A | 7/1995 | Smith et al. |
| 5,433,721 A | 7/1995 | Hooven et al. |
| 5,439,156 A | 8/1995 | Grant et al. |
| 5,447,265 A | 9/1995 | Vidal et al. |
| 5,452,836 A | 9/1995 | Huiteman et al. |
| 5,452,837 A | 9/1995 | Williamson, IV et al. |
| 5,458,279 A | 10/1995 | Plyley |
| 5,464,144 A | 11/1995 | Guy et al. |
| 5,465,894 A | 11/1995 | Clark et al. |
| 5,465,895 A | 11/1995 | Knodel et al. |
| 5,470,007 A | 11/1995 | Plyley et al. |
| 5,470,010 A | 11/1995 | Rothfuss et al. |
| 5,484,451 A | 1/1996 | Akopov et al. |
| 5,485,947 A | 1/1996 | Olson et al. |
| 5,487,500 A | 1/1996 | Knodel et al. |
| 5,489,058 A | 2/1996 | Plyley et al. |
| 5,497,934 A | 3/1996 | Brady et al. |
| 5,503,320 A | 4/1996 | Webster et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,937 A | 7/1996 | Boiarski et al. |
| 5,547,117 A | 8/1996 | Hamblin et al. |
| 5,549,628 A | 8/1996 | Cooper et al. |
| 5,551,622 A | 9/1996 | Yoon |
| 5,553,765 A | 9/1996 | Knodel et al. |
| 5,562,239 A | 10/1996 | Boiarski et al. |
| 5,562,241 A | 10/1996 | Knodel et al. |
| 5,564,615 A | 10/1996 | Bishop et al. |
| 5,575,803 A | 11/1996 | Cooper et al. |
| 5,580,067 A | 12/1996 | Hamblin et al. |
| 5,588,581 A | 12/1996 | Conlon et al. |
| 5,597,107 A | 1/1997 | Knodel et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,609,285 A | 3/1997 | Grant et al. |
| 5,624,452 A | 4/1997 | Yates |
| 5,630,541 A | 5/1997 | Williamson, IV et al. |
| 5,632,432 A | 5/1997 | Schulze et al. |
| 5,632,433 A | 5/1997 | Grant et al. |
| 5,634,584 A | 6/1997 | Okorocha et al. |
| 5,641,111 A | 6/1997 | Ahrens et al. |
| 5,655,698 A | 8/1997 | Yoon |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,665,085 A | 9/1997 | Nardella et al. |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,678,748 A | 10/1997 | Plyley et al. |
| 5,680,982 A | 10/1997 | Schulze et al. |
| 5,692,668 A | 12/1997 | Schulze et al. |
| 5,697,542 A | 12/1997 | Knodel et al. |
| 5,697,543 A | 12/1997 | Burdorff |
| 5,702,409 A | 12/1997 | Rayburn et al. |
| 5,704,534 A | 1/1998 | Huitema et al. |
| 5,716,366 A | 2/1998 | Yates |
| 5,725,554 A | 3/1998 | Simon et al. |
| 5,732,871 A | 3/1998 | Clark et al. |
| 5,735,848 A | 4/1998 | Yates et al. |

| | | | | | | |
|---|---|---|---|---|---|---|
| 5,752,965 | A | 5/1998 | Francis et al. | 6,045,560 A | 4/2000 | McKean et al. |
| 5,762,255 | A | 6/1998 | Chrisman et al. | 6,099,551 A | 8/2000 | Gabbay |
| 5,769,303 | A | 6/1998 | Knodel et al. | 6,131,789 A | 10/2000 | Schulze et al. |
| 5,769,892 | A | 6/1998 | Kingwell | 6,131,790 A | 10/2000 | Piraka |
| 5,779,132 | A | 7/1998 | Knodel et al. | 6,258,107 B1 * | 7/2001 | Balazs et al. ............... 606/153 |
| 5,785,232 | A | 7/1998 | Vidal et al. | 6,264,087 B1 | 7/2001 | Whitman |
| 5,794,834 | A | 8/1998 | Hamblin et al. | 6,315,183 B1 | 11/2001 | Piraka |
| 5,797,537 | A | 8/1998 | Oberlin et al. | 6,325,810 B1 | 12/2001 | Hamilton et al. |
| 5,810,240 | A | 9/1998 | Robertson | 6,544,271 B1 * | 4/2003 | Adams et al. ............. 606/139 |
| 5,810,811 | A | 9/1998 | Yates et al. | 6,585,144 B2 * | 7/2003 | Adams et al. ............ 227/175.1 |
| 5,810,855 | A | 9/1998 | Rayburn et al. | 7,032,799 B2 * | 4/2006 | Viola et al. ............. 227/175.1 |
| 5,820,009 | A | 10/1998 | Melling et al. | | | |
| 5,826,776 | A | 10/1998 | Schulze et al. | | FOREIGN PATENT DOCUMENTS | |
| 5,855,311 | A | 1/1999 | Hamblin et al. | | | |
| 5,871,135 | A | 2/1999 | Williamson, IV et al. | EP | 0625335 A1 | 11/1994 |
| 5,878,938 | A | 3/1999 | Bittner et al. | EP | 0639349 A2 | 2/1995 |
| 5,919,198 | A | 7/1999 | Graves, Jr. et al. | WO | WO 02/30297 A2 | 4/2002 |
| 5,988,479 | A | 11/1999 | Palmer | | | |
| 6,010,054 | A | 1/2000 | Johnson et al. | * cited by examiner | | |

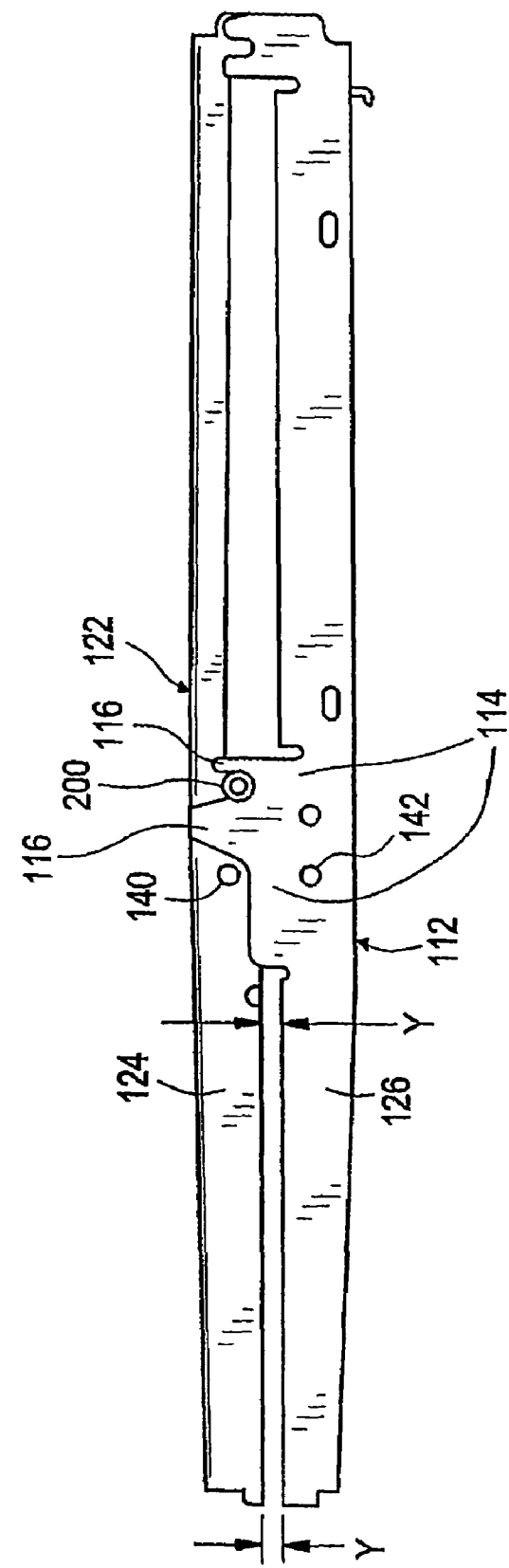

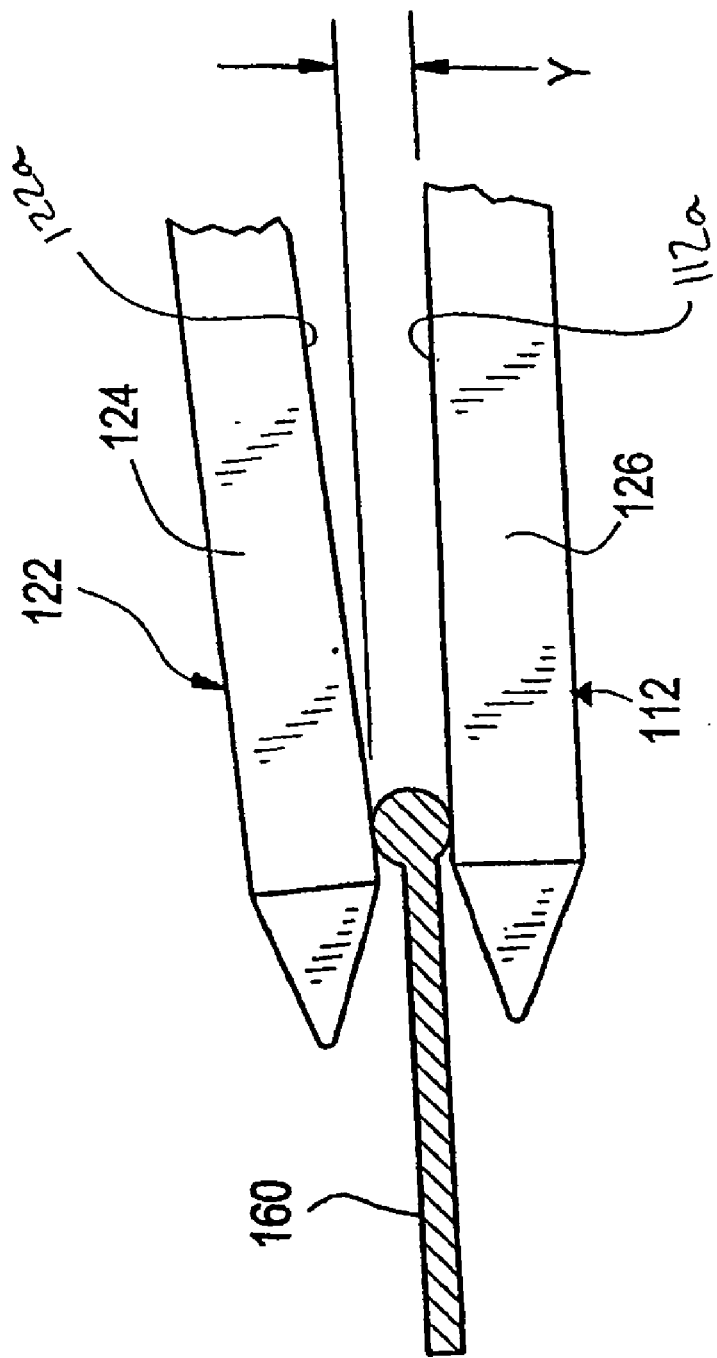

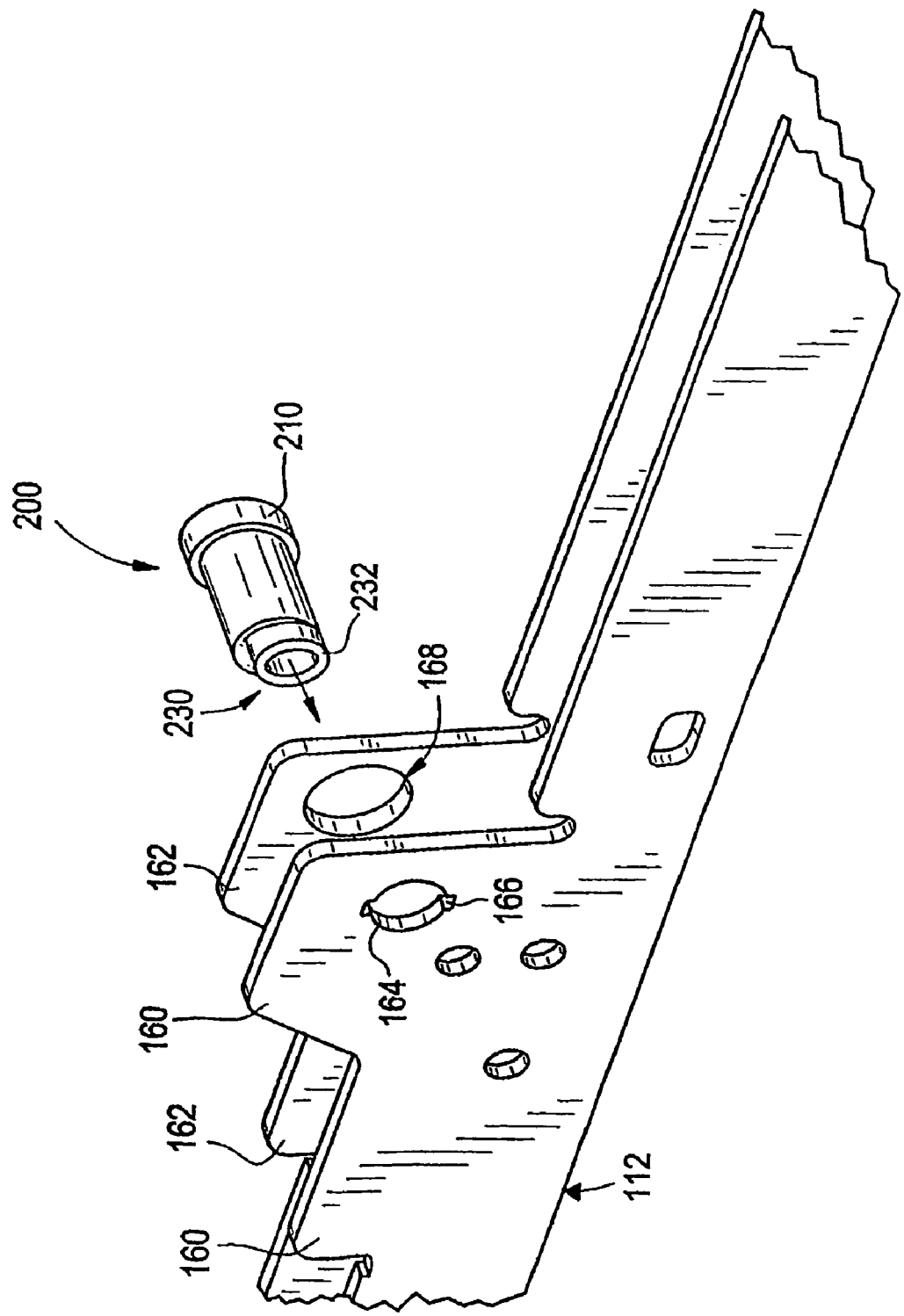

SURGICAL STAPLING APPARATUS AND METHOD

CROSS-REFERENCE TO RELATED APPLICATIONS

This application is a divisional of U.S. patent application Ser. No. 10/490,517 filed Mar. 23, 2004 now U.S. Pat. No. 7,032,799, which is a national of PCT Ser. No. PCT/US2002/31963 filed Oct. 4, 2002, which claims priority to U.S. Provisional Patent Application Ser. No. 60/327,369 filed Oct. 5, 2001, the disclosures of which are incorporated herein in their entirety by this reference.

BACKGROUND

1. Technical Field

The present disclosure relates to surgical stapling apparatus and, more particularly to staple-gap adjustment members for use in surgical stapling apparatus.

2. Background of Related Art

Surgical devices wherein tissue is first grasped or clamped between opposing jaw structures and then joined by means of surgical fasteners are well known in the art. In some such instruments a knife is provided to cut the tissue which has been joined by the fasteners. The fasteners are typically in the form of surgical staples however, other surgical fasteners may also be utilized, such as, for example, clips or two part polymeric surgical fasteners.

Instruments for applying surgical fasteners typically include two elongated beam members which are respectively used to capture or clamp tissue therebetween. Typically, one of the beam members carries a disposable cartridge which houses a plurality of staples arranged in at least two lateral rows while the other beam member comprises an anvil which defines a surface for forming the staple legs as the staples are driven from the cartridge. Where two part fasteners are used, this beam member carries the mating part, e.g. the receiver, to the fasteners driven from the cartridge. Generally, the staple formation process is effected by the interaction between a longitudinally moving camming surface and a series of individual staple pusher members. As the camming surface travels longitudinally through the cartridge carrying member, the individual pusher members are biased laterally, thus acting upon the staples to individual pusher members are biased laterally, thus acting upon the staples to sequentially eject them from the cartridge. A knife may travel with the pusher between the staple rows to longitudinally cut the tissue between the rows of formed staples. Examples of such instruments are disclosed in U.S. Pat. Nos. 3,079,606 and 3,490,675.

A later stapler disclosed in U.S. Pat. No. 3,499,591 applies a double row of staples on each side of the incision. This is accomplished by providing a cartridge assembly in which a cam member moves through an elongate guide path between two sets of staggered staple carrying grooves. Staple drive members are located within the grooves and are positioned in such a manner so as to be contacted by the longitudinally moving cam to effect ejection of the staples.

It is desired and it is a main objective of the present disclosure to provide improved surgical fastener applying apparatus, and to provide improved mechanisms and methods for producing improved surgical fastener applying apparatus, which apparatus have a uniform fixed staple gap that is consistently within a narrow range, well within the acceptable staple gap tolerance range, and that consistently produces formed staples that are within a narrow range well within the acceptable staple tolerance range.

Accordingly, the need exists for surgical fastener applying apparatus which has a uniform fixed staple gap that is consistently within a narrow range and that will remain uniform during a firing stroke. In addition, the need exists for a surgical fastener applying apparatus which will not fire if a disposable staple cartridge is not properly loaded within the apparatus or is not loaded in the apparatus at all or will not fire if the surgical fastener applying apparatus is in an unclamped state. The continuing need exists for a surgical fastener applying apparatus which will not accept a completely fired or a partially fired disposable staple cartridge therein.

SUMMARY

It is desired and it is a main objective of this invention to provide improved surgical staplers, and to provide improved mechanisms and methods for producing improved surgical staplers, which staplers have a uniform fixed staple gap that is consistently within a narrow range, well within the acceptable staple gap tolerance range, and that consistently produces formed staples that are within a narrow range well within the acceptable staple tolerance range.

It is also an object of the invention to produce surgical staplers that, when sold for use, or prior to use, have virtually no variations in staple gap from stapler to stapler of a given model and that provide improved staples.

The present disclosure is directed to linear staple-gap adjustment members for use in surgical stapling apparatus. The present disclosure is also directed to methods of adjusting and fixing the staple gap of a surgical stapling apparatus.

In accordance with one aspect of the present disclosure, a staple gap adjustment member, for use in a surgical stapling apparatus having a pair of jaw structures operably coupled with one another and defining a staple gap therebetween, includes one or more bearing portions sharing a common rotational axis, and one or more cam surface portions having a periphery with at least two different points along the periphery. Preferably, each point along the periphery has a different radius from the rotational axis.

It is envisioned that the one or more cam surface portions has a central axis parallel to and spaced a distance from the rotational axis of the one or more bearing portions. It is contemplated that the one or more bearing portions are configured and adapted to be disposed and locked in mounting plates formed in one of the pair of jaw structures. The one or more cam surface portions are configured and adapted to contact an opposed surface of the other of the pair of jaw structures. According, rotation of the gap adjustment member, about the rotational axis, causes the staple gap between the pair of jaw structures to vary in distance.

It is contemplated that a recess is formed in at least one end of the bearing or cam surfaces. The recess is configured and adapted to receive a complementary shaped rotational tool therein. It is envisioned that the recess can have a shape which is polygonal, conical, slotted, cruciform, torx, circular and/or irregular. The one or more bearing surfaces preferably each have either a circular, oval, elliptical or polygonal cross-section.

A 180° rotation of the gap adjustment member results in an adjustment in the size of the staple gap equal to about twice the distance between the rotational axis of the one or more bearing surfaces and the central axis of the one or more cam surfaces. Preferably, the staple gap adjustment member is configured and adapted to create an adjustment in the size of the staple gap. Alternatively it is envisioned that cam adjustment members which create staple gap adjustment by their linear, e.g. horizontal motion, e.g. a wedge, can be employed.

In another embodiment, the staple gap adjustment member includes a forward portion, a rearward portion and a body portion. Preferably, the forward and rearward portions share a common rotational axis. The body portion interconnects the forward and rearward portions and has a periphery with at least two different points therealong. Preferably, each point has a different radius from the rotational axis. It is contemplated that the body portion has a central axis parallel to and spaced a distance from the rotational axis of the forward and rearward portions.

It is envisioned that the forward and rearward portions of the gap adjustment member are configured and adapted to be disposed in mounting plates formed in one of the pair of jaw structures. It is further envisioned that the body portion of the gap adjustment member is configured and adapted to contact an opposed surface of the other of the pair of jaw structures. The forward and rearward portions of the gap adjustment member are preferably configured and adapted to be locked in the mounting plates. Rotation of the gap adjustment member about the rotational axis causes the staple gap between the pair of jaw structures to vary in distance.

It is contemplated that a recess is formed in at least one of the forward and rearward portions. The recess is configured and adapted to receive a complementary shaped rotational tool therein. The shape of the recess is at least one of polygonal, conical, slotted, cruciform, torx, circular and irregular. The forward, rearward and body portions each have either a circular, oval, elliptical or polygonal cross-section. Preferably, a 180° rotation of the gap adjustment member results in an adjustment in the size of the staple gap equal to about twice the distance between the rotational axis of the forward and rearward portions and the central axis of the body portion.

In accordance with another aspect of the present disclosure there is provided a surgical stapling apparatus including a jaw structure with a cartridge receiving portion and a jaw structure with an anvil receiving portion. The jaw structures are operably couplable to one another to provide a staple gap between a forward portion of the cartridge receiving and anvil receiving portions. Preferably, one of the jaw structures has a pair of mounting members thereon for mounting the other of the jaw structures thereon.

The surgical stapling apparatus further includes a staple gap adjustment member operatively disposed between the jaw structures. A rotation of the gap adjustment member results in a corresponding adjustment in the size of the staple gap. It is envisioned that the gap adjustment member includes one or more bearing portions sharing a common rotational axis, and one or more cam surface portions having a periphery with at least two different points along the periphery, with each point along the periphery having a different radius from the rotational axis. In an alternative embodiment, it is envisioned that the gap adjustment member includes a central axis parallel to and spaced a distance from the rotational axis of the one or more bearing portions.

It is contemplated that the staple gap adjustment member can include a forward portion, a rearward portion, and a body portion. The forward and rearward portions preferably share a common rotational axis. The body portion interconnects the forward and rearward portions and preferably has a periphery with at least two different points along the periphery. Preferably, each point along the periphery has a different radius from the rotational axis. In one embodiment it is envisioned that the body portion has a central axis spaced a distance from the rotational axis of the forward and rearward portions.

Preferably, the mounting members of the surgical stapling apparatus are configured and dimensioned to rotatably receive the gap adjustment member thereon. One of the jaw structures includes a pair of substantially parallel spaced apart mounting plates extending therefrom. The pair of mounting plates are configured and dimensioned to rotatably receive the gap adjustment member thereon.

Preferably, the gap adjustment member is coupled to the pair of mounting plates via a snap-fit type engagement and that the body portion of the gap adjustment member extends between the pair of mounting plates. It is envisioned that the other of the pair of jaw structures, not having the pair of mounting plates, is configured and dimensioned to be disposed between the pair of mounting plates and to rest atop the body portion of the gap adjustment member.

Rotation of the gap adjustment member, about the rotational axis, causes the pair of jaw structures to displace relative to one another and in turn causes the staple gap between the cartridge receiving portion and the anvil receiving portion to vary in size. A 180° rotation of the gap adjustment member results in an adjustment of the size of the staple gap equal to about twice the distance between the rotational axis of the forward and rearward portions and the central axis of the body portion.

It is envisioned that the surgical stapling apparatus further includes a plurality of gauging elements each having a different predetermined fixed thickness. The plurality of gauging elements are selectively insertable in the staple gap to set the staple gap to a size equal to the thickness of a selected gauging element.

It is envisioned that the staple gap adjustment member is fixedly secured to at least one of the jaw structures, preferably, to at least one of the pair of mounting members.

The present disclosure also provides for methods of adjusting a staple gap in a surgical stapling apparatus. A method of the present disclosure includes the steps of inserting a gauging element into a staple gap defined between the forward portions of a respective first and second jaw structure, adjusting the size of the staple gap by manipulating a gap adjustment member disposed between the first and second jaw structures to approximate the size of the staple gap to the size of the gauging element and locking the gap adjustment member into position. In another aspect of the method, the gauging element is inserted between opposed tissue contacting surfaces of the first and second jaw structures.

Another method of the present disclosure includes the steps of providing a surgical stapling apparatus having a pair of jaw structures operably coupled with one another, providing a gap adjustment member between the pair of jaw structures, inserting a gauging element into the staple gap, manipulating the gap adjustment member in order to adjust the size of the staple gap, and locking the gap adjustment member into position. Preferably, the pair of jaw structures define a staple gap between opposed distal surfaces thereof. It is envisioned that the gap adjustment member includes one or more bearing portions sharing a common rotational axis and one or more cam surface portions having a periphery with at least two different points along the periphery. Preferably, each point along the periphery has a different radius from the rotational axis. In one aspect, the one or more cam surface portions has a central axis parallel to and spaced a distance from the rotational axis of the bearing portions.

It is contemplated that the gap adjustment member includes a forward portion, a rearward portion and an eccentric body portion. Preferably, the forward and rearward portions share a common rotational axis. The eccentric body portion preferably interconnects the forward and rearward portions to one another. The body portion has a central axis spaced a distance from the rotational axis of the forward and rearward portions. It is envisioned that the forward and rearward portion of the gap adjustment member is rotatably received in mounting plates formed in one of the first and second jaw members and the body portion extends between the mounting plates.

In yet another aspect of the present disclosure, the method of adjusting a staple gap includes providing a surgical stapling apparatus having a jaw structure with an anvil receiving portion and a jaw structure with a cartridge receiving portion, the jaw structures being operatively couplable to one another to provide a staple gap between a respective forward portion of the anvil and cartridge receiving portions, one of the jaw structures having a pair of mounting members thereon for mounting the other of the jaw structures thereon, positioning a gap adjustment member on the mounting members between the jaw structures to provide a desired gap between the forward portions of the anvil and cartridge receiving portions, and locking the gap adjustment member to the mounting members to provide the desired staple gap.

The method further includes the steps of inserting a gauging element into the staple gap and manipulating the gap adjustment member in order to adjust the size of the staple gap. Preferably, the gap adjustment member includes one or more bearing portions sharing a common rotational axis, and one or more cam surface portions having a periphery with at least two different points along the periphery, with each point along the periphery having a different radius from the rotational axis. It is contemplated that the one or more cam surface portions have a central axis parallel to and spaced a distance from the rotational axis of the one or more bearing portions.

Other objects and features of the present disclosure will become apparent from consideration of the following description taken in conjunction with the accompanying drawings.

BRIEF DESCRIPTION OF THE DRAWINGS

Preferred embodiments of the presently disclosed surgical stapling apparatus and method are described herein with reference to the drawings. It should be understood, however, that the drawings are designed for the purpose of illustration only and not as a definition of the limits of the invention.

FIG. 3 is a side elevational view of the typical surgical stapling apparatus shown in FIG. 2 with the separated parts joined together;

FIG. 6 is an enlarged side elevational view of the tip portion of the surgical stapling apparatus shown in FIG. 1 depicting the use of a gauging element disposed between opposed surfaces of a distal end of the surgical stapling apparatus according to the present disclosure;

FIG. 12 is an enlarged perspective view of the hinge plates of an alternative surgical stapling apparatus for receiving a gap adjustment member;

DETAILED DESCRIPTION OF PREFERRED EMBODIMENTS

Figure 1:
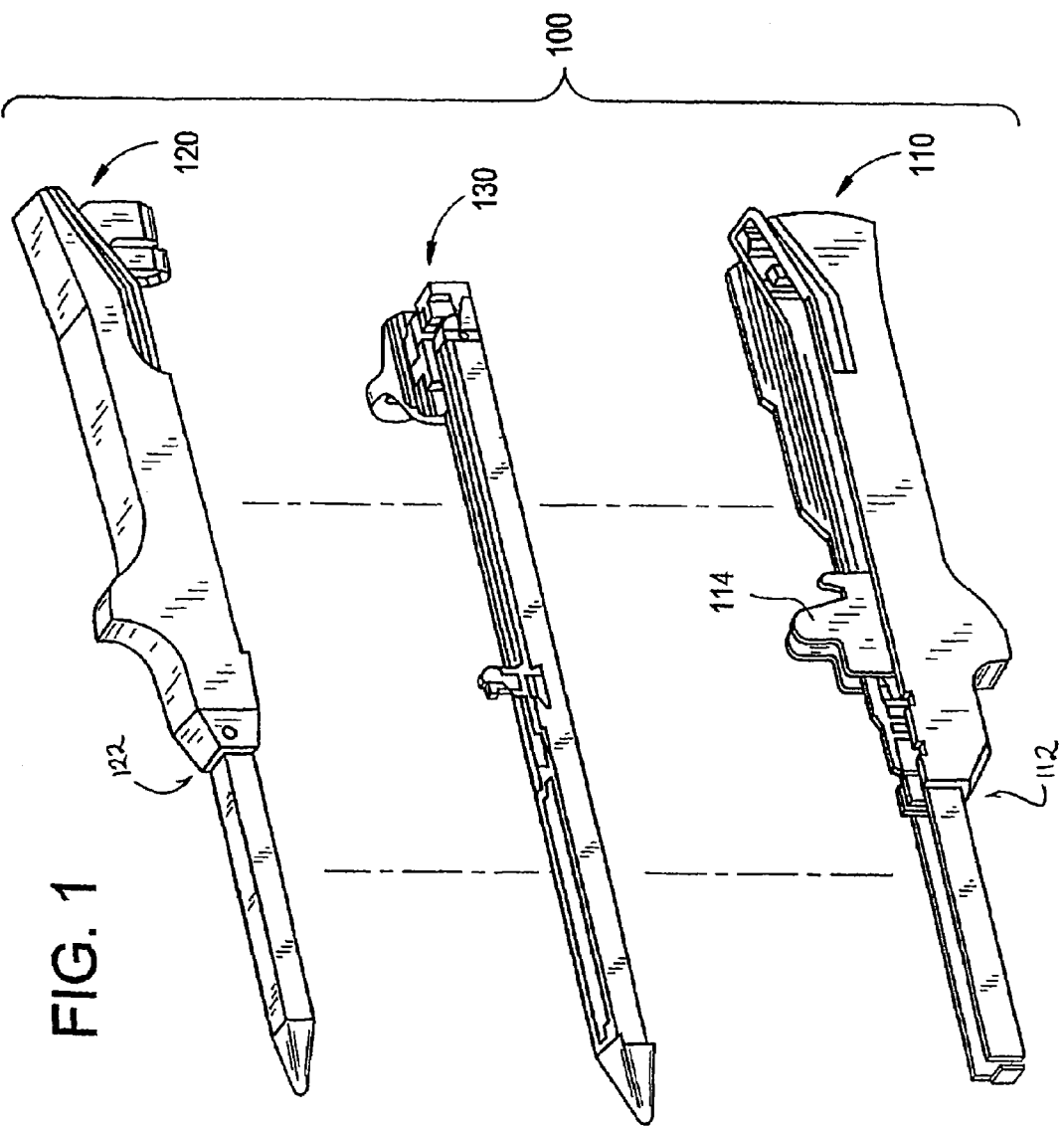
FIG. 1 is a perspective view depicting the separated parts of a surgical stapling apparatus according to the present disclosure.

Preferred embodiments of the presently disclosed linear stapler-gap adjustment mechanism will now be described in detail with reference to the accompanying drawings, in which like reference numerals designate identical or corresponding elements in each of the several views.

Figure 2:
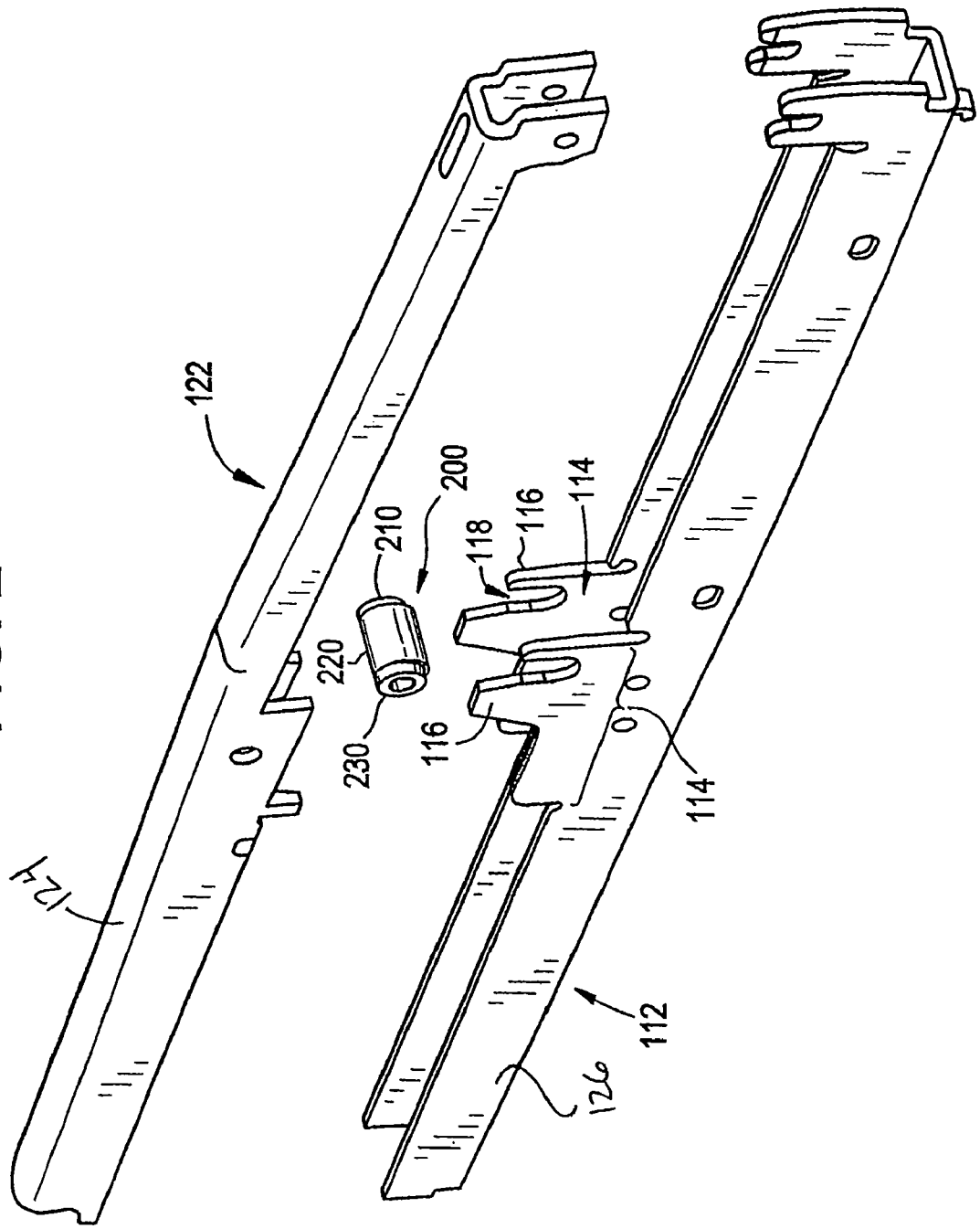
FIG. 2 is an enlarged perspective view of certain separated parts of a typical surgical stapling apparatus depicting the relative placement of one illustrative embodiment of a gap adjustment member, in accordance with the present disclosure, in portions of the surgical stapling apparatus.

Referring initially to FIGS. 1-3, a surgical stapling apparatus is generally shown as 100. Surgical stapling apparatus 100 includes a first jaw structure 110 having a cartridge receiving structure 112 adapted for receiving a cartridge assembly 130 and a second jaw structure 120 having an anvil receiving structure 122. The anvil (not shown) is attached, fixed or integral with anvil receiving structure 122. Cartridge receiving structure 112 includes a pair of mounting members, preferably mounting plates, here shown as upstanding hinge plates 114 for hingedly connecting first jaw structure 110 to second jaw structure 120. Each pair of hinge plates 114 includes a pair of uprights 116 defining a receiving recess 118 formed therein. Preferably, receiving recess 118 is configured and adapted to receive a gap adjustment member, here an eccentric cam 200, for example by a snap fit type connection.

Cartridge receiving structure 112 and anvil receiving structure 122 are coupled to one another via a pair of pivot pins, a first pivot pin 140 passing through the side walls of anvil receiving structure 122 and a second pivot pin 142 passing through the side walls of cartridge receiving structure 112. Pivot pins 140, 142 are interconnected by an internal linkage (not shown) having a fixed length, which linkage inhibits vertical movement of cartridge receiving structure 112 with respect to anvil receiving structure 122. The pair of pivot pins 140, 142 are disposed between the staple forming portion of the stapling apparatus and receiving recess 118 formed in the pair of hinge plates 114. In this manner, cartridge receiving structure 112 and anvil receiving structure 122 will pivot about pivot pins 140, 142.

Figure 5:
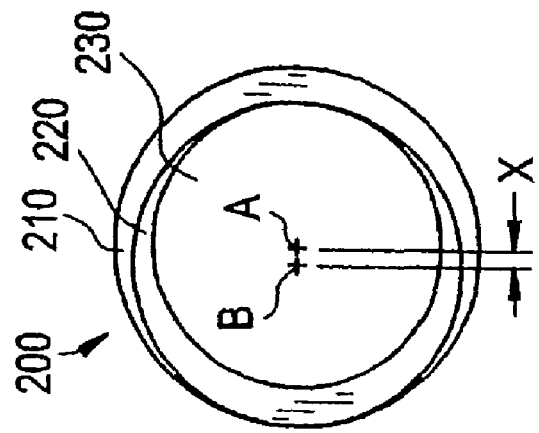
FIG. 5 is a rear elevational view of the illustrative gap adjustment member as shown in FIG. 2.
Figure 4:
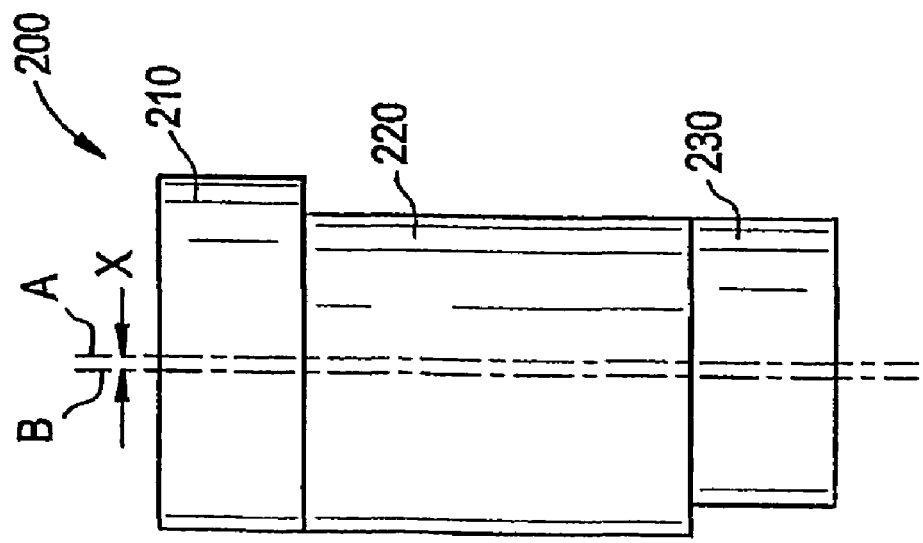
FIG. 4 is an enlarged side elevational view of the illustrative gap adjustment member as shown in FIG. 2.

As seen in FIGS. 2, 4 and 5, eccentric cam 200 includes a cylindrical forward portion 210, a cylindrical body portion 220 and a cylindrical rearward portion 230. Cylindrical forward portion 210 and cylindrical rearward portion 230 share a common central axis "A". While eccentric cam 200 is depicted, in FIG. 2, with forward portion 210 having a different diameter than rearward portion 230, it is envisioned that both forward portion 210 and rearward portion 230 can have the same diameter provided they share a common central axis. Body portion 220 has a central axis "B" spaced a distance "X" from central axis "A" of forward and rearward portions 210, 230. When body portion 220 is a cylinder, as forward and rearward portions 210, 230 rotate about common axis "A", body portion 220 acts like a cam which moves one or more objects placed on or engaging body portion 220 through a maximum distance "2X". While rotation of eccentric cam 200 results in a maximum distance of displacement of "2X" it is envisioned that eccentric cam 200 can be dimensioned to cause a displacement of any suitable distance upon a rotation thereof.

While body portion 220 has been shown and described as a cylinder, it is envisioned that body portion 220 can take on any other shape (e.g., an oval) which would define a camming surface and which other shape would determine the distance "X" through which the one or more objects placed on or engaging body portion 220 would move. For example, if the camming surface is not a cylinder, e.g., a tear drop shape, then the enlarged or cup portion of the tear drop would not be eccentric to axis "A." A cam is herein understood to be a structure having a periphery with at least two different points along the periphery, with each point having a different radius from the rotational axis. Cams utilizable in accordance with the present disclosure can be any suitable shape (e.g., triangular, oblong, tear drop and the like).

Returning to FIGS. 2 and 3, forward portion 210 and rearward portion 230 of eccentric cam 200 are configured and adapted to be received in the pair of receiving recesses 118 of hinge plates 114 while body portion 220 has a length substantially equal to the spacing between the interior surfaces of the pair of hinge plates 114. Since forward and rearward portions 210, 230 are disposed within a respective receiving recess 118, forward and rearward portions 210, 230 are considered bearing structures. Moreover, anvil receiving structure 122 is configured and adapted to be disposed between the pair of hinge plates 114 and to sit on and ride atop body portion 220 of eccentric cam 200. In this manner, as eccentric cam 200 is rotated about common axis "A" of forward and rearward portions 210, 230, body portion 220 presses against anvil receiving structure 122, rotating a rearward portion of anvil receiving structure 122 about pivot pin 140, thereby altering the spatial distance between anvil receiving structure 122 and cartridge receiving structure 112 by a maximum distance "2X". Since body portion 220 causes the displacement of anvil receiving structure 122 and cartridge receiving structure 112 relative to one another, body portion 220 is considered the camming structure. It is envisioned that surgical stapling apparatus 100 can be modified such that body portion 220 is considered the bearing structure and forward and rearward portions 210, 230 are considered the camming structures.

Figure 6A:
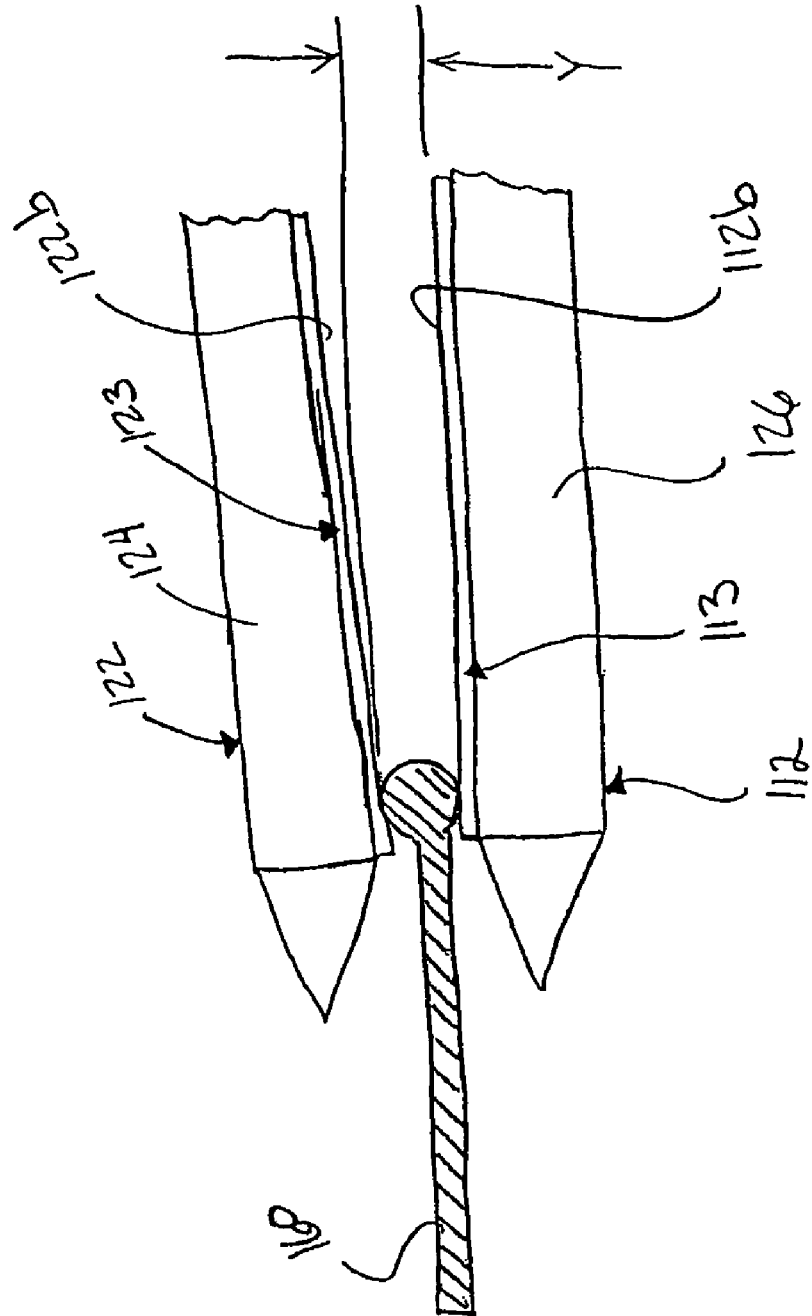
FIG. 6A is an enlarged side elevational view of the tip portion of the surgical stapling apparatus shown in FIG. 1 depicting the use of a gauging element disposed between the tissue contacting surfaces of the distal end of the surgical stapling apparatus.

Eccentric cam 200 provides surgical stapling apparatus 100 with a simple adjustment member whereby a spatial distance or gap "Y" (FIGS. 3 and 6) between a forward portion 126 of cartridge receiving structure 112 and a forward portion 124 of anvil receiving structure 122 can be adjusted and set to an accurate predetermined distance regardless of the incoming tolerances or variations resulting from the manufacturing and or assembly process of the individual components of surgical stapling apparatus 100. In other words, gap "Y", between forward portion 126 of cartridge receiving structure 112 and forward portion 124 of anvil receiving structure 122, can be set to a narrow tolerance due to the adjustability provided by eccentric cam 200 irrespective of whether the individual components of surgical stapling apparatus 100 are manufactured with a wide tolerance. Preferably, as seen in FIG. 6, gap "Y" is measured between an upper surface or face 112a of cartridge receiving structure 122 and an opposed lower surface or face 122a of the anvil receiving structure 122, along the length of the forward portion of the stapler. The forward portion of the stapler is considered that portion of the stapler that is distal of hinge plates 114 and that encompasses or includes the working longitudinal extent or portion of the cartridge and anvil. Alternatively, as seen in FIG. 6A, gap "Y" is measured between a tissue contacting surface 112b of a cartridge assembly 113 which is disposed within cartridge receiving structure 126, and a tissue contacting surface 122b of an anvil member 123 which is disposed within anvil receiving structure 122.

As seen in FIG. 6, after assembling most if not all of the individual components of the surgical stapling apparatus 100, gap "Y", for the forward portion of surgical stapling apparatus 100 is set. According to one method of setting gap "Y", a gauging element 160 having a predetermined fixed thickness is inserted into gap "Y" at the distal tip of surgical stapling apparatus 100. Eccentric cam 200 is fixed or then rotated until gap "Y" is set to the predetermined thickness of gauging means 160. Gap "Y" is set in an unloaded or loaded condition, preferably unloaded, i.e., without tissue present, or with some load. Other suitable means and methods can be employed at the same time or other times during or as part of the manufacturing or assembly process.

Eccentric cam 200 is adjusted until receiving structures 112, 122 contact gauging means 160. Once the position of eccentric cam 200 is fixed or set, eccentric cam 200 is fixedly secured or locked into position, by any suitable means, in recesses 118 such that further rotation of eccentric cam 200 is prevented. Typically, gap "Y" will be narrower at the distal tip and will be progressively wider from the distal tip to the hinge plates, such that in the loaded condition, with tissue present, deflection will occur at the tip to create a more uniform gap along the forward portion 124, 126 of surgical stapling apparatus 100. While the adjustment and the setting of gap "Y" is a step which is disclosed as taking place during the manufacture and assembly of surgical stapling apparatus 100, it is envisioned that the adjustment and setting of gap "Y" can be done post manufacturing and assembly, preferably prior to packaging of the stapler. It is also envisioned that, with certain embodiments, a minor adjustment can be made by the user.

Figure 7:
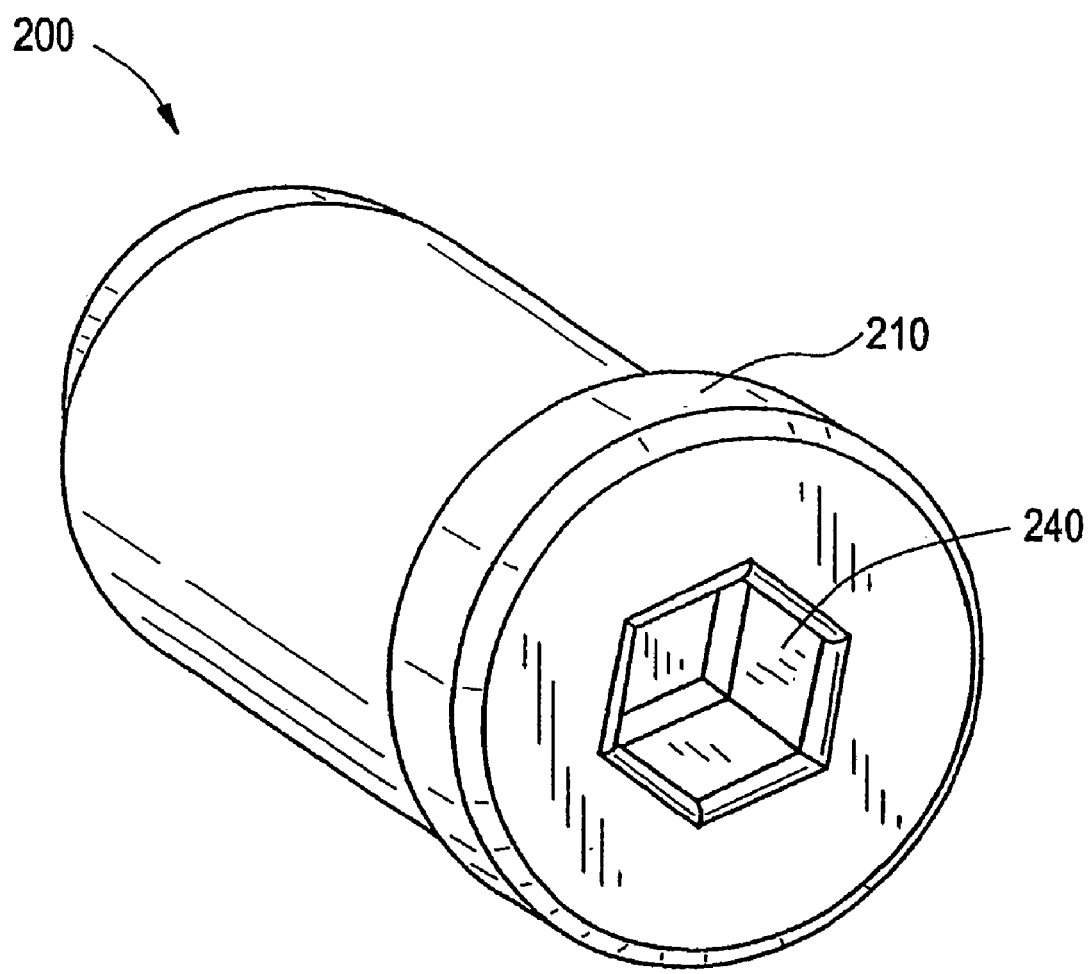
FIG. 7 is an enlarged perspective view of one embodiment of a gap adjustment member according to the present disclosure.

With reference to FIGS. 7-11, various means for rotating eccentric cam 200 are provided thereon and will now be described. As seen in FIG. 7, forward portion 210 of eccentric cam 200 is provided with a hexagonal recess 240 formed in an end or top surface thereof. Hexagonal recess 240 is configured to receive an "Allen Key" type end of a rotational tool (not shown) in order to rotate eccentric cam 200. While a hexagonal recess 240 is shown, it is envisioned that any polygonal recess (i.e., triangular, square, pentagonal, etc.) can be provided along with a rotational tool configured with a polygonal protrusion corresponding in shape to the polygonal recess formed in the end surface of forward portion 210.

Figure 8:
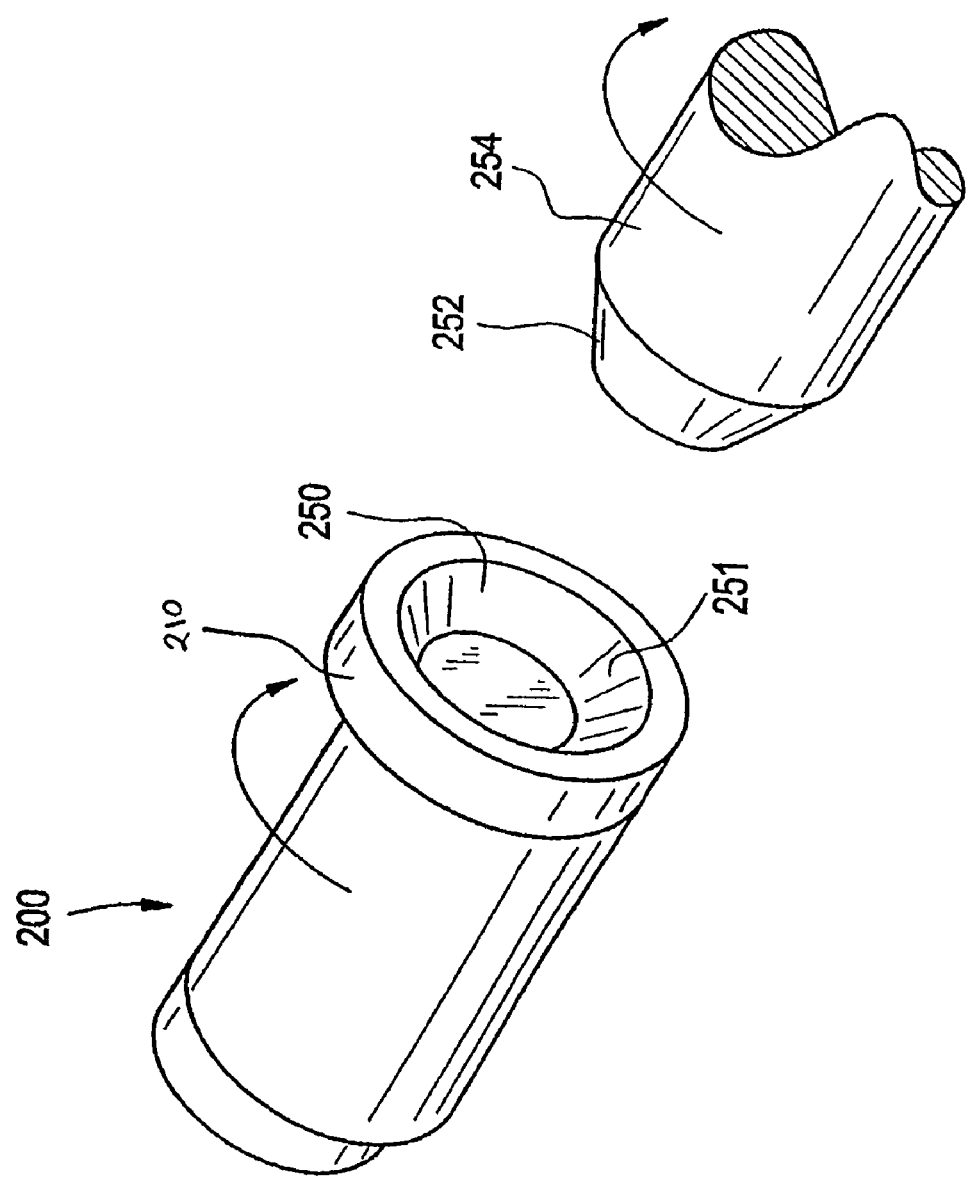
FIG. 8 is an enlarged perspective view of an alternative embodiment of a gap adjustment member according to the present disclosure.

As seen in FIG. 8, forward portion 210 of eccentric cam 200 is provided with a conical recess 250 formed in an end, top or outer surface thereof, wherein conical recess 250 preferably is provided with a roughened surface 251 for frictionally mating with a conical protrusion 252 extending from a distal end of a rotational tool 254.

Figure 9:
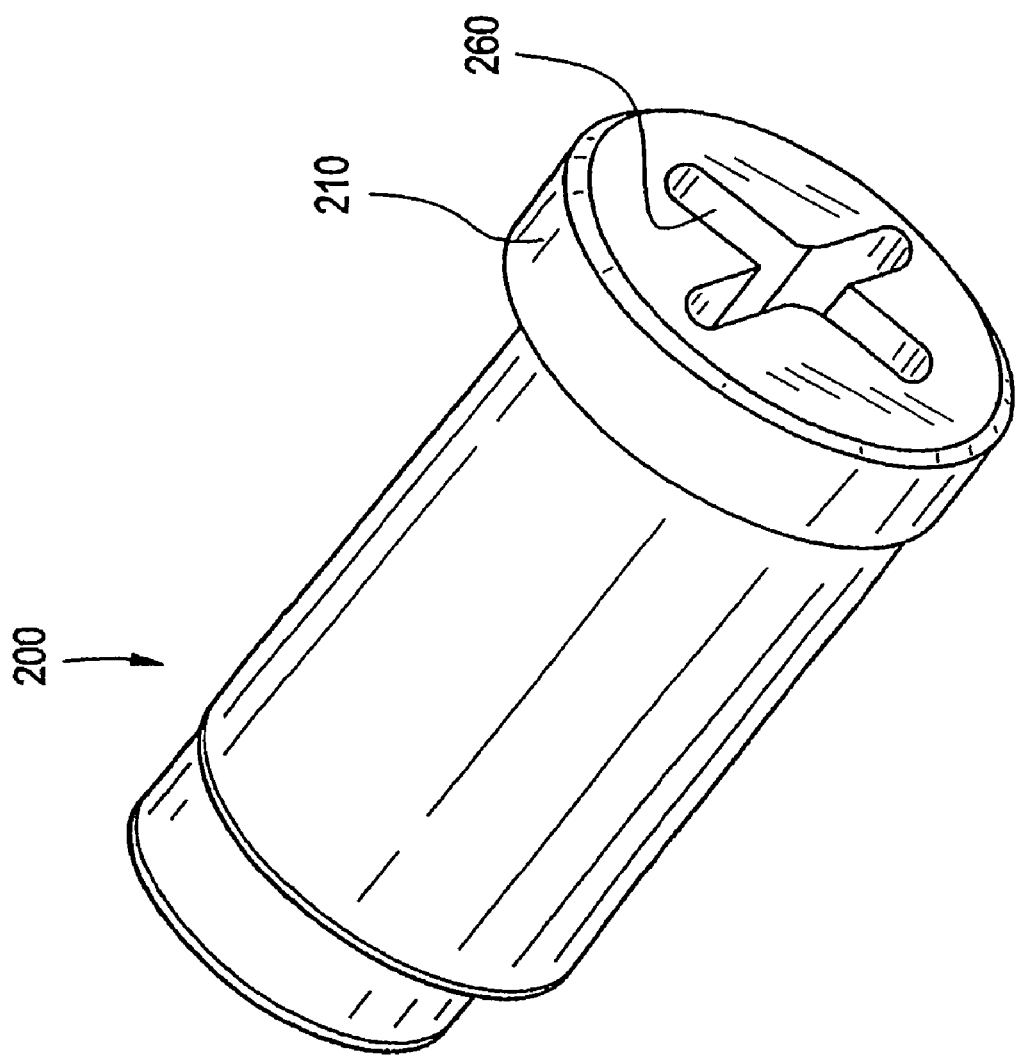
FIG. 9 is an enlarged perspective view of a further embodiment of a gap adjustment member according to the present disclosure.

As seen in FIG. 9, forward portion 210 of eccentric cam 200 is provided with a conventional screw driver recess 260 (i.e., slotted, cruciform or Phillips, torx, etc.) formed in an end, top or outer surface thereof. Screw driver recess 260 is configured to receive an end of a standard screw driver (not shown) in order to rotate eccentric cam 200.

Figure 10:
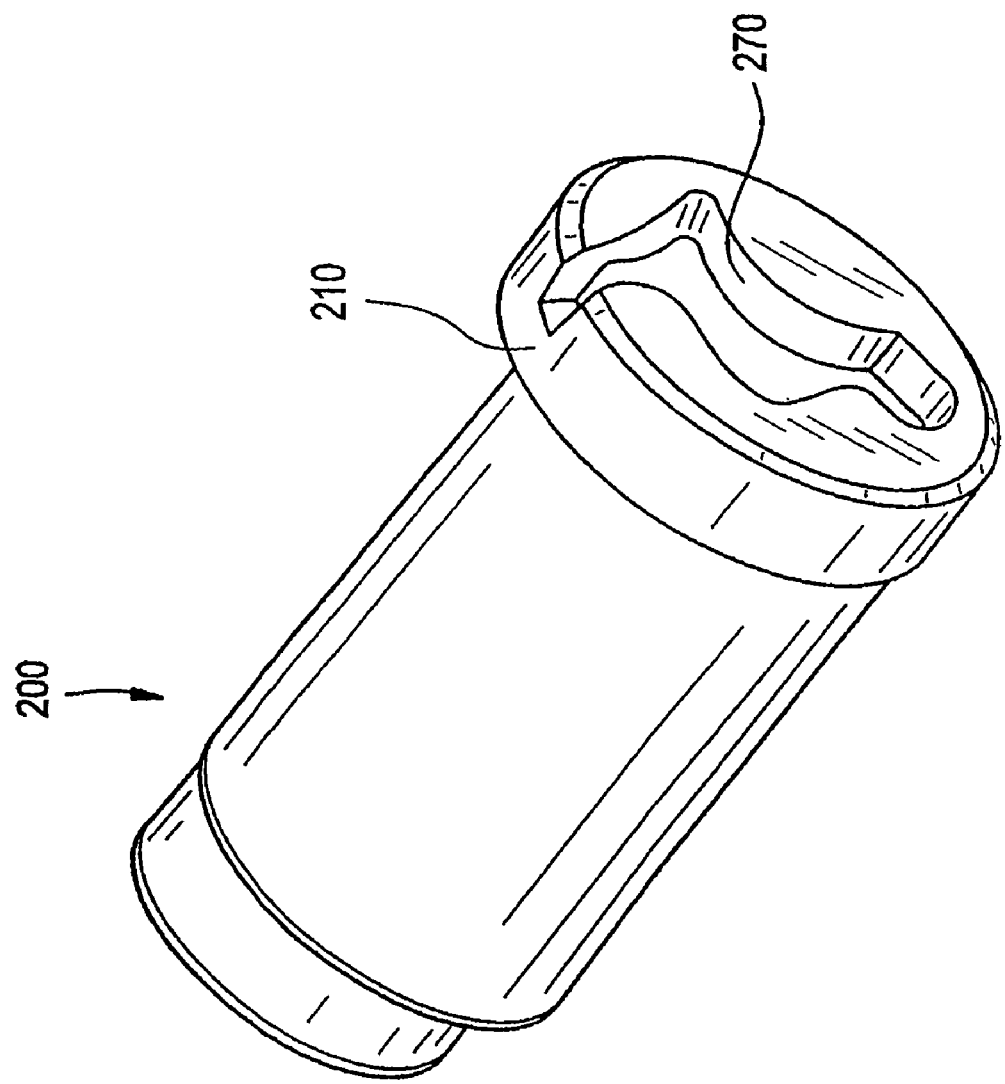
FIG. 10 is an enlarged perspective view of another embodiment of a gap adjustment member according to the present disclosure.

As seen in FIG. 10, forward portion 210 of eccentric cam 200 is provided with an irregularly shaped recess 270 formed in an end or top surface thereof. Irregularly shaped recess 270 can be formed having a portion which is located at a greater radius from rotational axis "A" of eccentric cam 200 than another portion of recess 270. In the same manner as the aforementioned recesses, a rotational tool (not shown) having a protrusion configured and adapted for cooperation with recess 270 is used in order to rotate eccentric cam 200.

Figure 11:
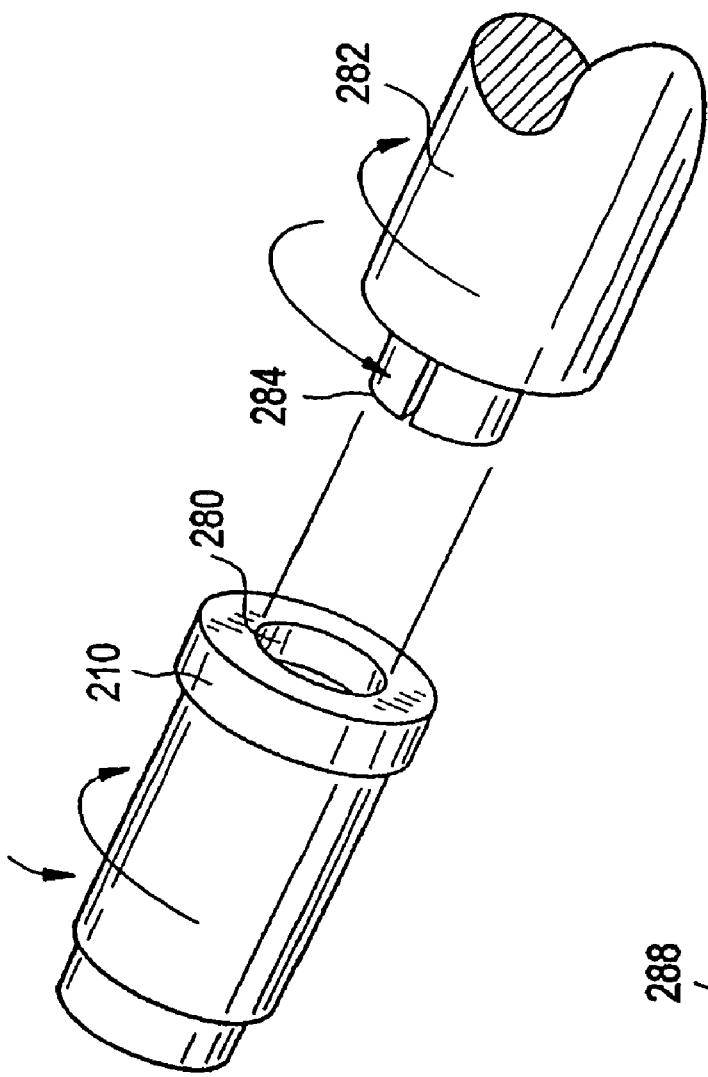
FIG. 11 is an enlarged perspective view of yet another embodiment of a gap adjustment member according to the present disclosure.
Figure 11A:
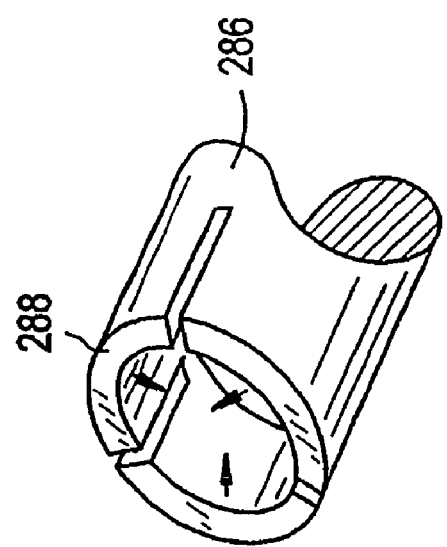
FIG. 11A is an enlarged perspective view of a distal end of a tool for engaging the gap adjustment member as shown in FIG. 11.

As seen in FIG. 11, forward portion 210 of eccentric cam 200 is provided with a circular recess 280 formed in an end or top surface thereof. An expandable portion of a rotational tool 282 is depicted having a cylindrical forward portion 284 which is expandable after insertion into circular recess 280 of eccentric cam 200. Expansion of cylindrical forward portion 284 of rotational tool 282, after insertion in circular recess 280, causes the outer surface of cylindrical forward portion 284 to press against the inner surface of circular recess 280 thereby enabling rotational tool 282 to transmit rotation to eccentric cam 200. Alternatively, as seen in FIG. 11A, a contractible rotational tool 286 can be provided, which contractible rotational tool 286 includes a cylindrical forward portion 288 which is contractible about the outer diameter of forward portion 210 of eccentric cam 200. Accordingly, contraction of cylindrical forward portion 288 of rotational tool 286, after placement about forward portion 210 of eccentric cam 200, causes the inner surface of cylindrical forward portion 288 to press against the outer surface of forward portion 210 of eccentric cam 200 thereby enabling rotational tool 286 to transmit rotation to eccentric cam 200.

While the recesses are located in and the methods and devices for rotating eccentric cam 200 are described as being effected relative to the top end or forward portion of eccentric cam 200, it is understood that the recesses can be located in and the methods and devices can be effected relative to either or both ends of eccentric cam 200.

Figure 13:
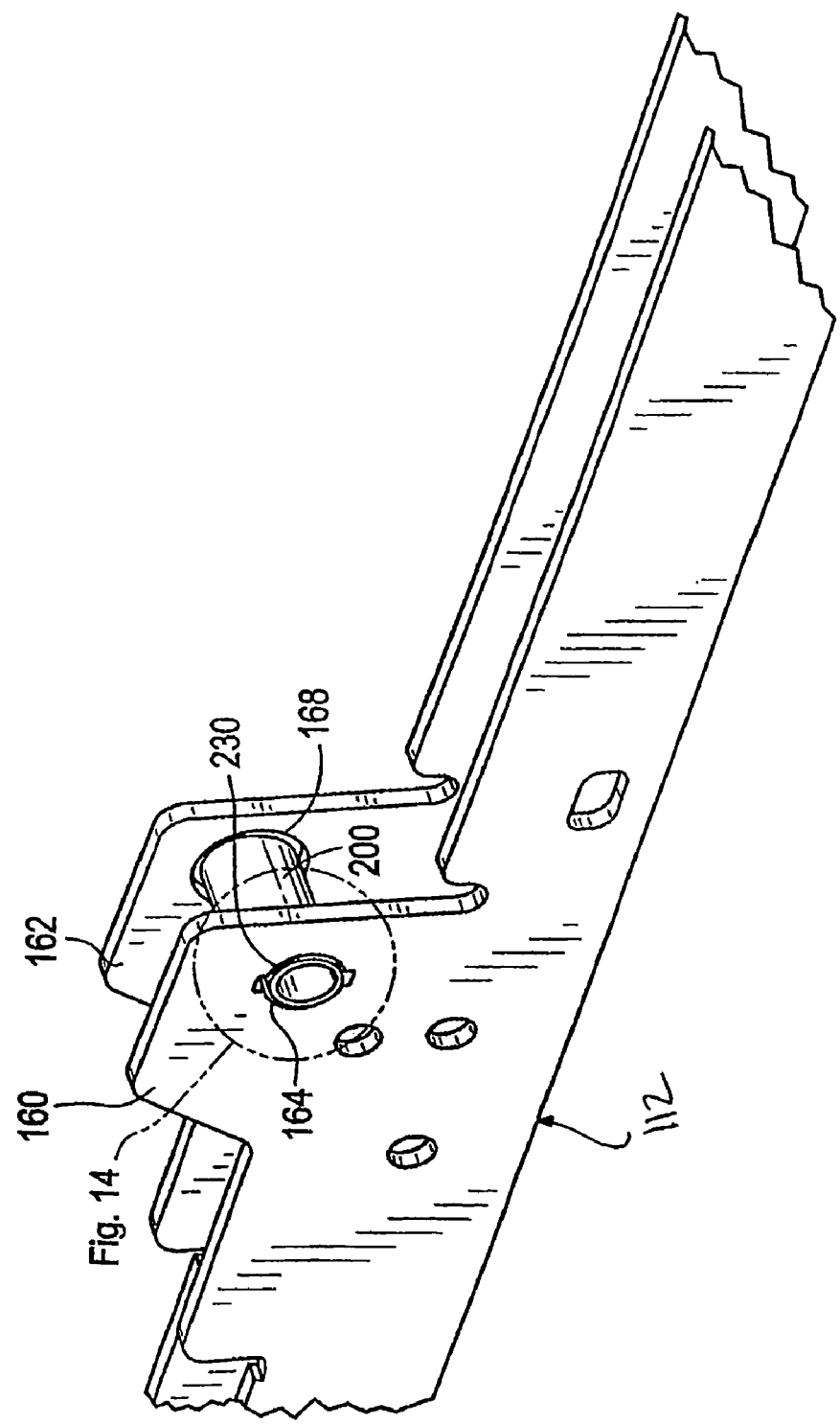
FIG. 13 is an enlarged perspective view of the hinge plates shown in FIG. 12 with the gap adjustment member shown in place.
Figure 14:
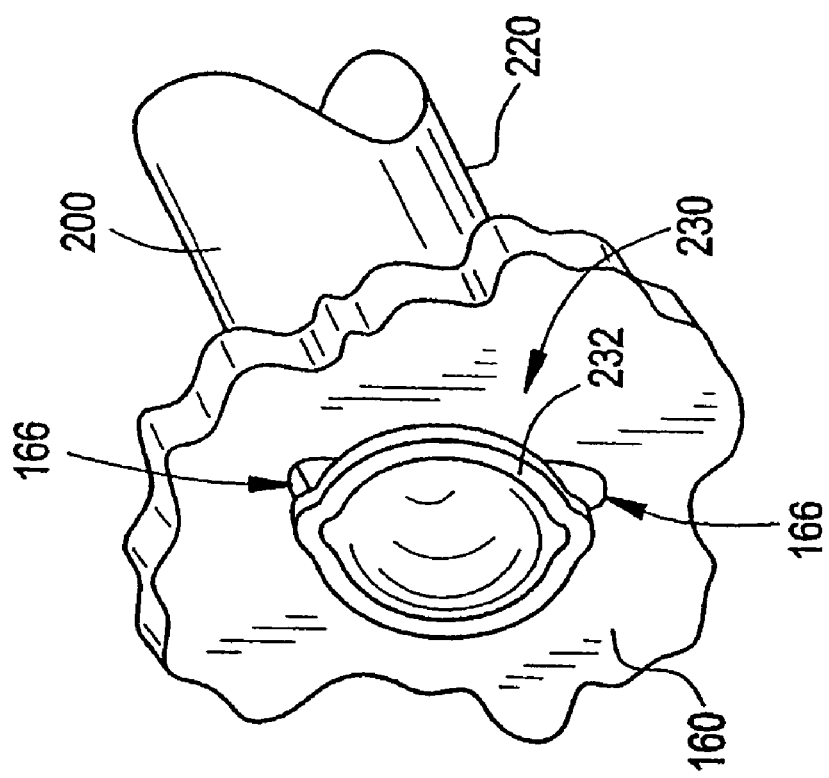
FIG. 14 is a detail of area "14" of FIG. 13 showing the securement of the gap adjustment member to the hinge plates.

Turning now to FIGS. 12-14, preferred methods of securely fixing an eccentric cam to a stapling apparatus are disclosed. According to a preferred method, a pair of hinge plates are disclosed for use with an eccentric cam 200 having a rearward portion 230 defined by an annular wall 232. As seen in FIG. 12, cartridge receiving structure 112 is provided with a first upstanding hinge plate 160 and a second upstanding hinge plate 162 each extending from the side surface of the cartridge receiving structure 112. First hinge plate 160 is provided with a through hole 164 having at least one notch 166 formed into a circumferential perimeter thereof and sized to snugly receive a portion of rearward portion 230 of eccentric cam 200 thereinto or therethrough. Second hinge plate 162 is provided with a through hole 168 that is sized to snugly receive forward portion 210 of eccentric cam 200 thereinto or therethrough. FIG. 13 is intended to depict eccentric cam 200 snugly in place within the pair of through holes 164, 168. FIG. 14 is intended to show that after eccentric cam 200 has been rotated to the desired position, eccentric cam 200 is fixedly secured or locked in place by deforming annular wall 232 tightly into notches 166 formed along the circumferential perimeter of through-hole 164.

Figure 15:
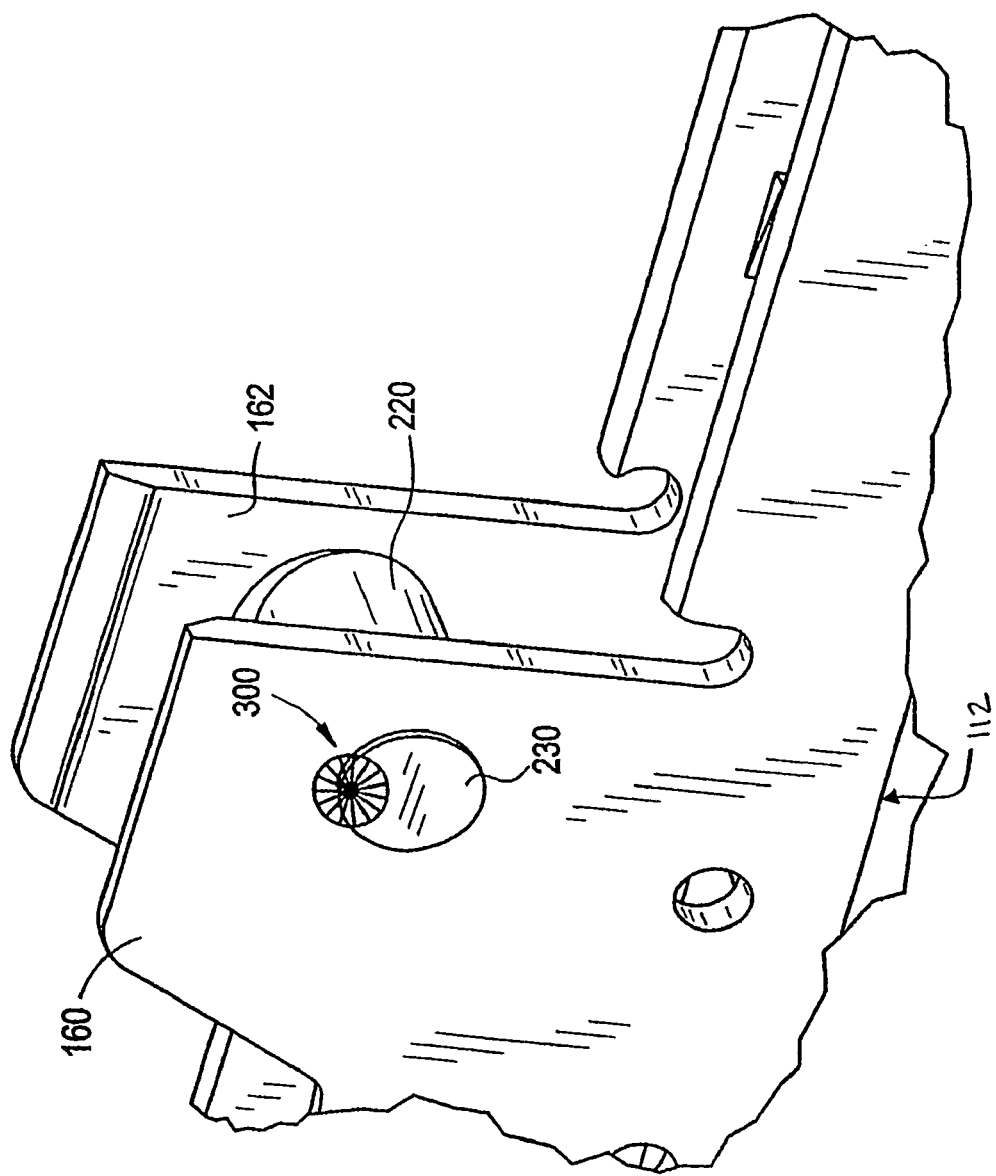
FIG. 15 is an enlarged perspective view depicting the securement of the gap adjustment member to the hinge plates according to an alternative method.
Figure 16:
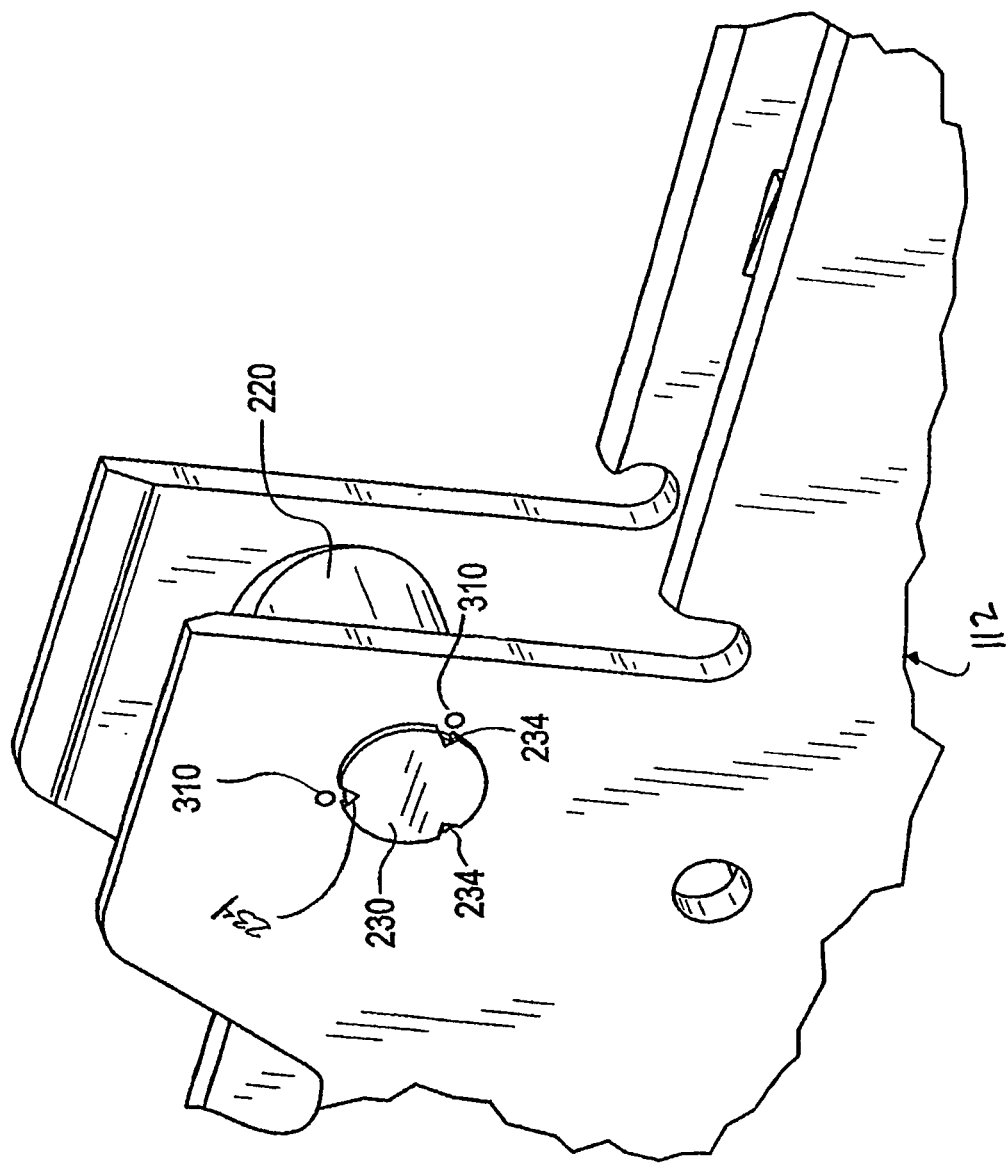
FIG. 16 is an enlarged perspective view depicting the securement of the gap adjustment member to the hinge plates according to another method.
Figure 17:
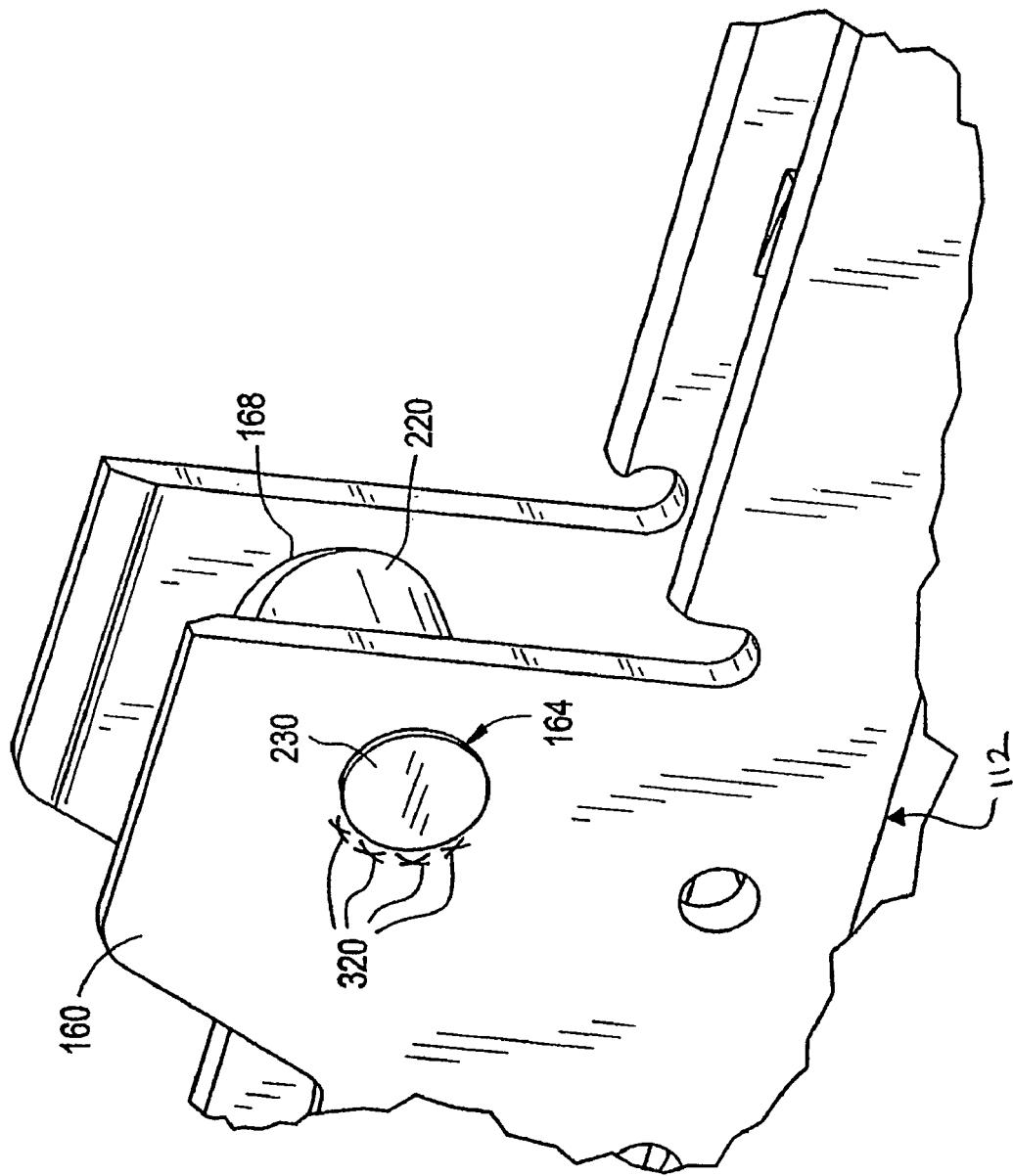
FIG. 17 is an enlarged perspective view depicting the securement of the gap adjustment member to the hinge plates according to yet another method.

Turning now to FIGS. 15-17, alternative methods of securely fixing eccentric cam 200 to the pair of hinge plates 160, 162 are described. As seen in FIG. 15, rearward portion 230 of eccentric cam 200 is securely fixed in place by one or more spot welds 300 (i.e., metal-inert-gas "MIG", tungsten-inert-gas "TIG", arc, laser, sonic, electron beam, braze, silver solder, soft solder, etc.) between rearward portion 230 and hinge plate 160. As seen in FIG. 16, eccentric cam 200 can be securely fixed in place by a deformation 310 of a portion of the sheet metal of first hinge plate 160 (e.g., by pining, peening, swaging, center punching, etc.) into at least one, preferably each of recesses 234 formed along the circumference of rearward portion 230. As seen in FIG. 17, eccentric cam 200 can be securely fixed in place with one or more peenings 320 around rearward portion 230 of eccentric cam 200 until rearward portion 230 expands sufficiently to fill and restrict through-hole 164 to prevent the rotation of eccentric cam 200 therein. It is also envisioned that the sheet metal of hinge plate 160 can be peened around through-hole 164 until the sheet metal tightly grips rearward portion 230 of eccentric cam 200. Alternatively, any suitable adhesive or bonding agent, e.g., an anaerobic adhesive, such as Loctite™ (Trademark of American Sealants Company, Corp.) or equivalents, or other adhesive type fluid cements can be applied between the surface of forward and rearward portion 210, 230 and through-holes 164, 168, respectively.

Figure 18:
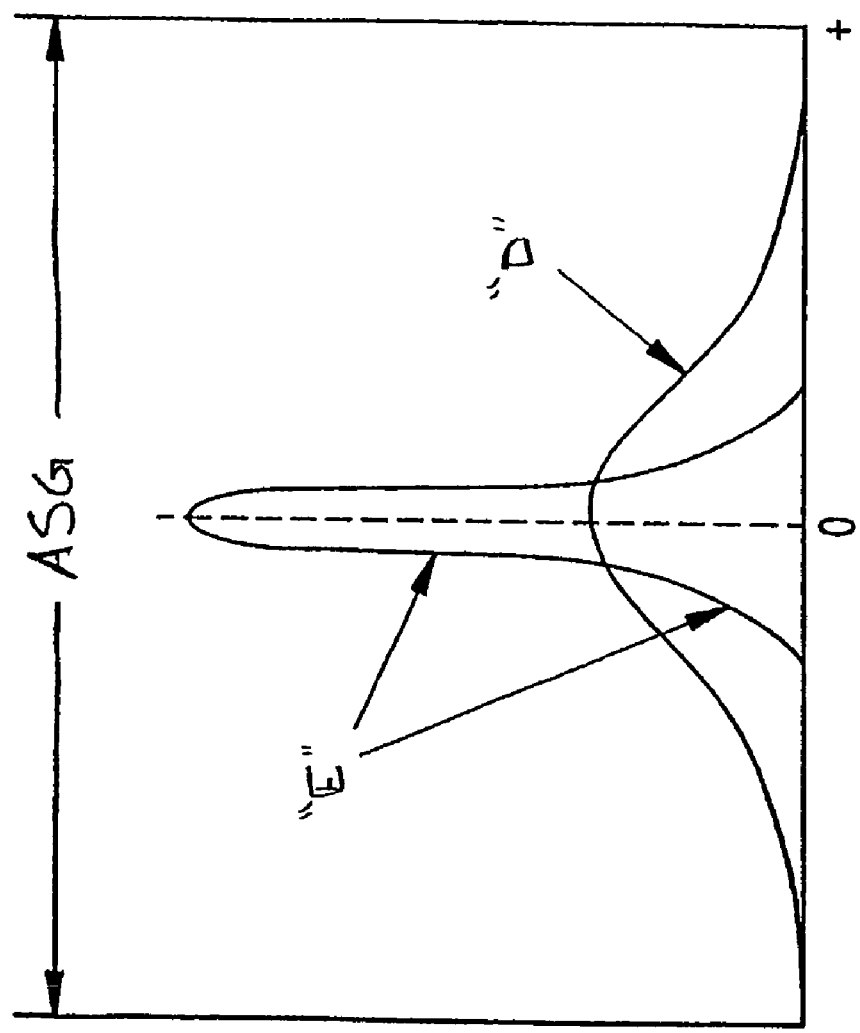
FIG. 18 is a schematic graphical representation of the current state of the art of the range of acceptable staple gaps as compared to the range of staple gaps in accordance with the present invention.

As seen the graph in FIG. 18, the acceptable staple gaps for surgical staplers manufactured according to the current state of the art as compared to those manufactured according to the present disclosure is shown. The current state of the art results in the manufacture and assembly of surgical staplers having a wide variation in the range of the resulting staple gap. During the manufacture and assembly of a specific line or model of surgical staplers, due to various factors inherent or involved in the manufacture and assembly of the surgical staplers, e.g., variations in materials, dimensions and conditions, there has been a wide variation in the size of staple gap "Y" within the acceptable staple gap "ASG" tolerance range, as depicted by the bell-shaped curve "D" in FIG. 18. However, in accordance with the present disclosure, despite the various factors disclosed above, manufactured and assembled surgical staplers can consistently have a narrower range of variations well within the acceptable range, as depicted by the bell-shaped curve "E" in FIG. 18. Thus, surgical staplers manufactured and assembled in accordance with the present disclosure have staple gaps which are more consistent and uniform than staple gaps of surgical staplers manufactured or produced in accordance with the current state of the art.

While it is shown that eccentric cam 200 is fixed or secured to one hinge plate, it is envisoined that eccentric cam 200 can be secured to both hinge plates. In addition, while a circular cam has been disclosed, it is envisoined that other types of camming members can be used without departing from the scope of the disclosure, for example, a ramp can be disposed between the cartridge receiving structure and the anvil receiving structure, a bendable tab can be configured, affixed to one of the structure and adapted to move the cartridge receiving structure relative to the anvil receiving structure, and one or more jack screws can be employed to move to contact the anvil receiving structure. Moreover, the present disclosure is especially suitable for linear surgical staplers, however, it is envisioned that the present disclosure is not solely limited to linear surgical staplers.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A method of adjusting a staple gap in a surgical stapling apparatus including a first and a second jaw structure each having a forward portion, an intermediate portion and a rear portion where the first and second jaw structures are joined, the first and second jaw structures being hingedly connected at a connection region of the intermediate portion spaced distally from where the first and second jaw structures are joined, the method comprising the steps of:
    inserting a gauging element into a staple gap defined between the forward portions of a respective first and second jaw structure, the first and second jaw structures being operably coupled to one another;
    adjusting the size of the staple gap by manipulating a gap adjustment member disposed between the first and second jaw structures at the intermediate portion of the respective first and second jaw structures adjacent the connection region, to approximate the size of the staple gap to the size of the gauging element; and
    locking the gap adjustment member into position.

2. The method according to claim 1, wherein the gauging element is inserted between opposed tissue contacting surfaces of the first and second jaw structures.

3. A method of adjusting a staple gap in a surgical stapling apparatus comprising the steps of:
    providing a surgical stapling apparatus having a pair of jaw structures operably couple with one another, the pair of jaw structures defining a staple gap between opposed distal surfaces thereof;
    providing a gap adjustment member between the pair of jaw structures, the gap adjustment member including one or more bearing portions sharing a common rotational axis and one or more cam surface portions having a periphery with at least two different points along the periphery, with each point along the periphery having a different radius from the rotational axis;
    inserting a gauging element into the staple gap;
    manipulating the gap adjustment member in order to adjust the size of the staple gap; and
    locking the gap adjustment member into position.

4. The method according to claim 3, wherein the one or more cam surface portions has a central axis parallel to and spaced a distance from the rotational axis of the bearing portions.

5. The method according to claim 3, wherein the gap adjustment member includes:
    a forward portion;
    a rearward portion, the forward and rearward portions sharing a common rotational axis; and
    an eccentric body portion interconnecting the forward and rearward portions, the body portion having a central axis spaced a distance from the rotational axis of the forward and rearward portions, wherein the forward and rearward portion of the gap adjustment member is rotatably received in mounting plates formed in one of the first and second jaw members and wherein the body portion extends between the mounting plates.

6. A method of adjusting a staple gap in a surgical stapling apparatus defining an intermediate portion, comprising the steps of:
    providing a surgical stapling apparatus having a jaw structure with an anvil receiving portion and a jaw structure with a cartridge receiving portion, the jaw structures being operatively couplable to one another to provide a staple gap between a respective forward portion of the anvil and cartridge receiving portions, one of the jaw structures having a pair of mounting members thereon for mounting the other of the jaw structures thereon, wherein the pair of mounting members are disposed at the intermediate portion of the surgical stapling apparatus spaced distally from a rear portion where the jaws structures are joined;
    positioning a rotatable gap adjustment member on the mounting members between the jaw structures to provide a desired gap between the forward portions of the anvil and cartridge receiving portions; and
    locking the gap adjustment member to the mounting members to-provide the desired staple gap.

7. The method according to claim 6 further comprising the steps of:
    inserting a gauging element into the staple gap; and
    manipulating the gap adjustment member in order to adjust the size of the staple gap.

8. The method according to claim 6, wherein the gap adjustment member is locked into position by at least one of deforming, pining, peening, swagging, center punching, welding and adhering the gap adjustment member against at least one of the mounting members.

* * * * *